United States Patent
Tan et al.

(10) Patent No.: US 9,464,312 B2
(45) Date of Patent: Oct. 11, 2016

(54) SCHIFF-BASE CONJUGATE OF N, N-DIBUTYL-P-PHENYLENEDIAMINE WITH PYRIDOXAL 5'-PHOSPHATE FOR IMPROVED HOMOCYSTEINE ASSAYS USING PYRIDOXAL 5'-PHOSPHATE-DEPENDENT ENZYMES

(71) Applicant: AntiCancer, Inc., San Diego, CA (US)

(72) Inventors: Yuying Tan, San Diego, CA (US); Shukuan Li, San Diego, AZ (US)

(73) Assignee: AntiCancer, Inc., San Diego, CA (US)

(*) Notice: Subject to any disclaimer, the term of this patent is extended or adjusted under 35 U.S.C. 154(b) by 0 days.

(21) Appl. No.: 14/152,784

(22) Filed: Jan. 10, 2014

(65) Prior Publication Data

US 2014/0193801 A1    Jul. 10, 2014

Related U.S. Application Data

(60) Provisional application No. 61/751,047, filed on Jan. 10, 2013.

(51) Int. Cl.
*C12Q 1/00* (2006.01)
*C12Q 1/527* (2006.01)
*C07F 9/58* (2006.01)

(52) U.S. Cl.
CPC .............. *C12Q 1/527* (2013.01); *C07F 9/582* (2013.01)

(58) Field of Classification Search
None
See application file for complete search history.

(56) References Cited

PUBLICATIONS

Tan et al., Nature Protocols, 2008, vol. 3, No. 9, p. 1388-1394.*

* cited by examiner

*Primary Examiner* — Kade Ariani
(74) *Attorney, Agent, or Firm* — Schmeiser, Olsen & Watts (57) ABSTRACT

A composition, method and kit for performing a two-reagent enzymatic homocysteine assay, wherein a single homocysteinase enzyme and a Schiff-based conjugate of N,N-dibutyl-p-phenyldiamine (DBPDA) with pyridoxal 5'-phosphate (PLP) are used to measure total homocysteine in plasma or serum. The assay measures a chromophore reaction product of $H_2S$ and the DBPDA released from the Schiff-base conjugate in the presence of a $Fe^{+3}$ containing compound. The resulting chromophore may be measured absorbance or fluorescence spectrophotometry.

11 Claims, 8 Drawing Sheets

SCHIFF-BASE CONJUGATE OF N, N-DIBUTYL-P-PHENYLENEDIAMINE WITH PYRIDOXAL 5'-PHOSPHATE FOR IMPROVED HOMOCYSTEINE ASSAYS USING PYRIDOXAL 5'-PHOSPHATE-DEPENDENT ENZYMES

FIELD OF TECHNOLOGY

The following relates to compositions, methods and kits for quantitatively determining the amount of total homocysteine in plasma or serum and evaluating the risk for diseases based on the measured quantity of total homocysteine present. More specifically, the following discloses embodiments directed toward a two-reagent enzymatic homocysteine assay utilizing homocysteinase and a Schiff-based conjugate of N,N-dibutyl-p-phenylenediamine with pyridoxal 5' phosphate.

BACKGROUND

Cardiovascular disease has the highest mortality in the US, causing one million heart attack and stroke deaths each year. More and more studies have reported that it is total homocysteine (tHCY) that plays a critical role in heart disease and stroke, as well as numerous other diseases. Hyperhomocysteinemia is a major risk factor of death of cardiovascular disease in patients with end-stage renal disease (ESRD) and plasma tHCY may be used as a new tumor marker to monitor cancer patients during chemotherapy. It has been reported that Alzheimer's disease patients and individuals with diabetes may have significant elevated plasma tHCY. In other diseases such as Parkinson's disease, homocysteine may play a role in sensitizing dopaminergic neurons to dysfunction and death. The concentration of tHCY may also be associated with common pregnancy complications and adverse pregnancy outcomes. Measuring tHCY levels routinely may assist physicians over the course of the pregnancy in monitoring the health of the fetus and the mother.

Various methods have been developed for measuring total homocysteine (tHCY) in plasma. These various methods include tHCY enzyme conversion immunology assays designed for the Abbott IMx analyzer, a microtiter plate tHCY enzymatic immunoassay, high performance liquid chromotography (HPLC) methods assays using multiple enzymes, and gas chromatography-mass spectrometry methods. These methods however, are complex, require highly specialized equipment to perform and have limited throughput. While a simpler four-reagent single-enzyme assay has been developed that does not require the specialized equipment of previous methods, the four-reagent assay is still more complicated than the assay disclosed herein. The four reagent assay includes additional reagents and steps in order to measure tHCY. The four reagent method is more expensive, requires more time to provide accurate readings, and is not applicable to most automated robotic analyzers currently in use. Thus there is a need for a tHCY assay that can measure the amount of tHCY that is simpler, cheaper, faster, and easier to perform than previous methods.

SUMMARY

An embodiment of the present disclosure relates to a method of measuring total homocysteine and comprises the steps of providing homocysteine, reducing the homocysteine with a reducing agent, enzymatically reacting the homocysteine with homocysteinase (HCYase), producing hydrogen sulfide ($H_2S$), providing N,N-dibutyl-p-phenylenediamine-pyridoxal 5'-phosphate (DBPDA-PLP Schiff-base), combining DBPDA-PLP, released from the Schiff-base, with the $H_2S$ in the presence of an Fe(III) containing compound, producing at least one chromophore, and measuring the at least one chromophore with a spectrophotometer or a fluorescence reader (fluorometer).

Another embodiment of the present disclosure relates to a method of producing N,N-dibutyl-p-phenyldiamine-pyridoxal 5'-phosphate comprising the steps of providing a solution of N,N-dibutyl-p-phenyldiamine (DBPDA) in anhydrous alcohol, mixing the solution with a pyridoxal 5'-phosphate (PLP) solution, producing a mixture, forming a precipitate by adjusting the pH of the mixture to approximately 4 and centrifuging the precipitate.

A further embodiment of the present disclosure relates to an alternative method of producing N,N-dibutyl-p-phenyldiamine-pyridoxal 5'-phosphate comprising the steps of providing a solution of N,N-dibutyl-p-phenyldiamine (DBPDA) in anhydrous alcohol, adding the solution to a pyridoxal 5'-phosphate (PLP) solution, producing a mixture and crystallizing the mixture.

An embodiment of the present disclosure relates to a kit, said kit comprising a first reagent, the first reagent including a mixture of a reducing agent, homocysteinase (HCYase) and N,N-dibutyl-p-phenyldiamine-pyridoxal 5'-phosphate; a second reagent, the second reagent including an Fe(III) containing compound; a first buffer solution; and a second buffer solution.

Another embodiment of the present disclosure relates to a method for detecting the risk of a total homocysteine (tHCY) dependent adverse condition, the method comprising the steps of extracting plasma or serum containing homocysteine from a patient, reducing the bound homocysteine with a reducing agent, enzymatically reacting the homocysteine with homocysteinase (HCYase), producing hydrogen sulfide ($H_2S$), providing N,N-dibutyl-p-phenylenediamine-pyridoxal 5'-phosphate (DBPDA-PLP Schiff-base), combining DBPDA released from the Schiff-base with the $H_2S$ in the presence of an Fe(III) containing compound, producing at least one chromophore, and measuring the at least one chromophore with a spectrophotometer.

Yet another embodiment of the present disclosure relates to a composition, the composition comprising N,N-dibutyl-p-phenylenediamine conjugated to pyridoxal 5'-phosphate.

BRIEF DESCRIPTION OF THE DRAWINGS

Some of the embodiments will be described in detail, with reference to the following figures, wherein like designations denote like members, wherein.

DETAILED DESCRIPTION

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present disclosure will in no way be limited to the number of constituting components, the materials thereof, the shapes thereof, the relative arrangement thereof, etc., and are disclosed simply as an example of embodiments of the present disclosure.

As a preface to the detailed description, it should be noted that, as used in this specification and the appended claims, the singular forms "a", "an" and "the" include plural referents, unless the context clearly dictates otherwise.

Elevated tHCY in biological fluids may be a risk factor for adverse diseases that are known to exhibit abnormal levels of tHCY. A normal level of tHCY in biological fluids is approximately 5 to 15 µmol/L, and concentrations greater than 15 µmol/L may be considered abnormal. Adverse conditions and diseases for which an individual with increased tHCY concentrations may be at risk include, but are not limited to, cardiovascular disease (particularly in individuals who may have end-stage renal disease (ESRD)), heart disease, stroke, diabetes, depression, Parkinson's disease, Alzheimer's disease, and vitamin deficiencies, particularly deficiencies in $B_6$, $B_{12}$ and folate. The quantitative measurement of tHCY may also be useful as a tumor marker to monitor cancer patients during chemotherapy. Furthermore, the tHCY concentration in biological fluids may provide information regarding other various health-related issues such as stress, smoking and aging.

Figure 1:
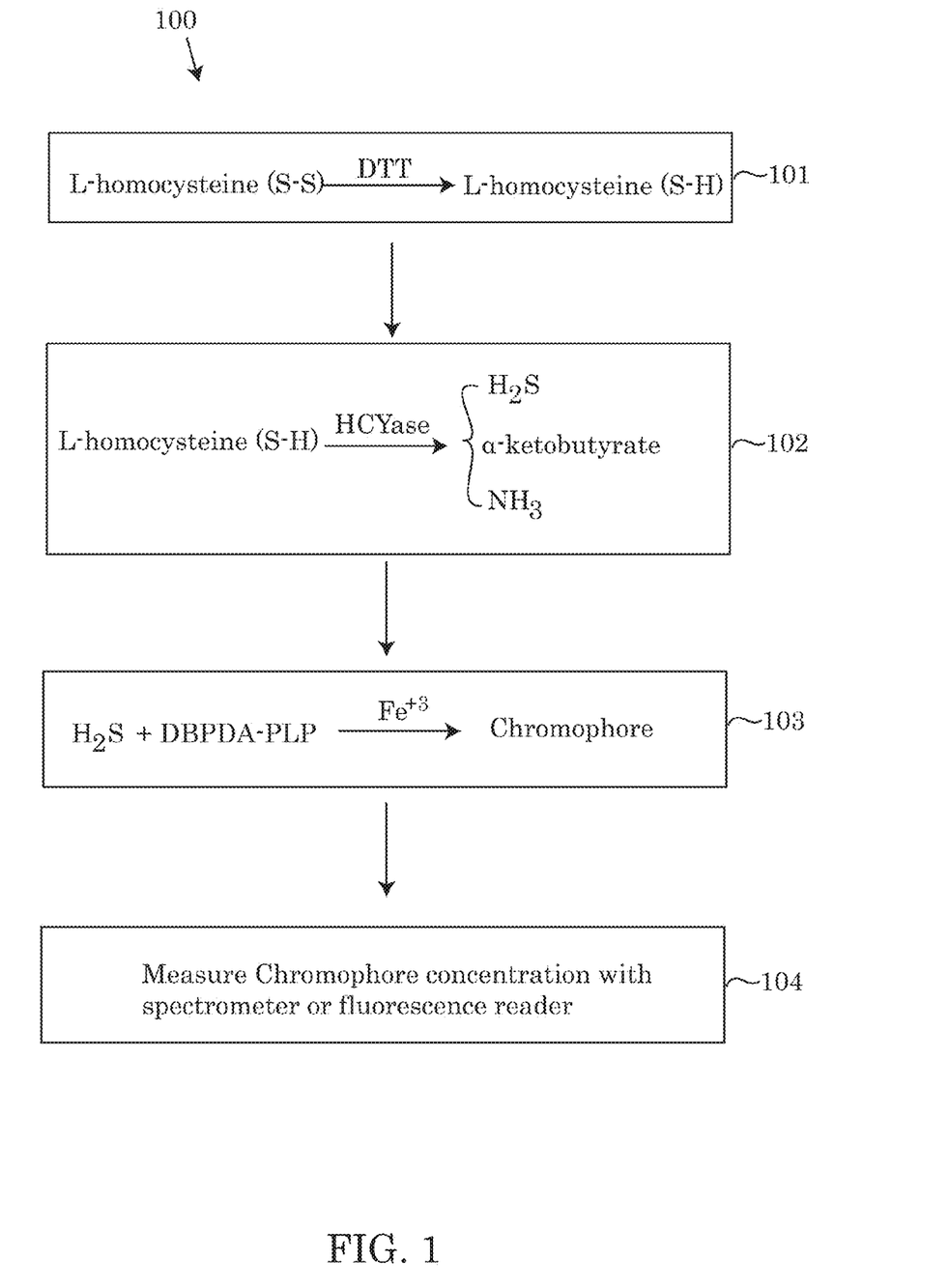
FIG. 1 depicts a flowchart describing an embodiment of a method for synthesizing a chromophore from homocysteine.

FIG. 1, depicts an embodiment of an Assay 100 for determining the total homocysteine (tHYC) concentration in biological fluids. Assay 100 measures the tHCY concentration of a biological fluid that contains homocysteine. The tHCY assay is used for in vitro diagnostics of biological samples. Some examples of biological fluids collected and analyzed using Assay 100 include urine, tissue fluid, blood, blood serum, or blood plasma. In the exemplary embodiment, EDTA or heparin-plasma/serum may be used for the tHCY assay. Red blood cells will synthesize tHCY after sampling, therefore the separation of plasma or serum from the blood cells should be performed within one hour. An alternative is use the inhibitor 3-deazaadenosine (3-DA) which will inhibit production of HCY by red blood cells and allow whole blood to be stored without separation for long periods. 3-DA does not interfere with HCYase and thus can be used with any embodiment of a tHCY assay that uses HCYase. Separation may be performed using centrifugation. In this example, the collected biological fluid may be centrifuged as 300×g for 5 minutes. In the one or more embodiments described herein, a minimum volume sample of 100 µl of biological fluid may be withdrawn. The biological fluid may be collected with or without EDTA or heparin. The biological sample should be kept cold (approximately 4-8° C.) until separation. The plasma/serum samples, under sterile conditions, may be stored at 4-8° C. for approximately four weeks. For longer storage periods, samples may be kept frozen at approximately −15 to −25° C. If the sample is not clear after thawing, the suspension may be removed by centrifugation and filtration before testing. Food consumption may affect circulating tHCY levels in the biological samples. Protein or fat-rich meals may result in a higher reported total tHCY value and should be avoided late in the day before sampling. Overnight fasting (for example 12 hours) before blood is drawn improves the accuracy of the tHCY assay.

In some embodiments of the Assay 100, the homocysteine measured may be the levorotatory isomer, L-homocysteine, which is the only isomer present in humans. L-homocysteine provided in the biological fluid may contain strong disulfide bonds. In some embodiments of the Assay 100, a reduction reaction 101 may be performed to reduce the disulfide (S—S) bonds to weaker sulfhydryl bonds (S—H). As depicted in FIG. 1, the reducing agent used to perform the reduction reaction 101 may be dithiothreitol (DTT). Other suitable reducing agents may include dithiobutylamine (DTBA), 3,3',3''-Phosphanetriyltripropanoic acid (TCEP), β-mercaptoethanol, cysteamine, bis(2-mercaptoethyl)sulfone (BMS), 2,3-dimercapto-1-propanol, cysteine ethyl ester, cysteine methyl ester, or any other compound known to reduce disulfide bonds to sulfhydryl bonds.

Embodiments of Assay 100 may determine tHCY concentrations in biological samples by enzymatically producing hydrogen sulfide ($H_2S$) from homocysteine. In one embodiment, a single homocysteine enzyme may be used. The enzyme may be any form of homocysteinase. "Homocysteinase" may be defined as any enzyme capable of catalyzing a reaction whereby $H_2S$ is produced from homocysteine. In one embodiment, the Assay 100 utilizes a highly specific recombinant homocysteinase, L-homocysteine α,γ-lyase (rHCYase). In another embodiment of the Assay 100, the homocysteinase is derived from *Trichomonas vaginalis* or *Pseudomonas* species, including, but not limited to, *ovalis* or *putida*. For example, the homocysteinase L-methionine-alpha-dearnino-gamma-mercaptomethane(methionine)lyase derived from *Pseudomonas putida* may be used. (The *P. putida* enzyme is problematic, however, because it also degrades cysteine, also releasing $H_2S$, thereby interfering in the assay since cysteine is present in blood at higher concentrations then HCY).

In other embodiments, homocysteinase may also be provided as a chimeric nucleotide sequence of either DNA or RNA, derived from more than one gene that codes for a chimeric homocysteinase enzyme. A chimeric homocysteinase enzyme may contain amino acid sequences corresponding to multiple sources, for example both *Trichomonas vaginalis* and *Pseudomonas putida*. The purified and isolated DNA molecule comprising a chimeric nucleotide sequence that encodes amino acid sequence of *Pseudomonas putida* homocysteinase, and amino acid sequence of *Trichomonas vaginalis* homocysteinase (derived from either mgl1, or mgl2, or both) may be expressed as functional proteins having homocysteinase activity. Such a chimeric enzyme not react with cysteine).

Embodiments of the enzymatic reaction 102 between homocysteine and HCYase result in the formation of $H_2S$, and in some embodiments may further include the formation of additional side products. Side products of the enzymatic reaction 102 include ammonia and α-ketobutyrate. In the exemplary embodiments, $H_2S$ is the enzymatic reaction product that is measured to determine the tHCY concentration. In alternative embodiments however, other products of the enzymatic reaction such as ammonia and/or α-ketobutyrate may be detected and measured to determine the tHCY concentration.

In the exemplary embodiments of the assay 100, $H_2S$ is not directly measured to calculate tHCY concentration. Instead, a chromophore-producing reaction 103 is performed, wherein the resulting chromophore is measured. The chromophore measurement indirectly indicates the amount of $H_2S$ produced from the enzymatic reaction 102, which directly correlates with the concentration of tHCY present in the biological fluid.

Figure 2:
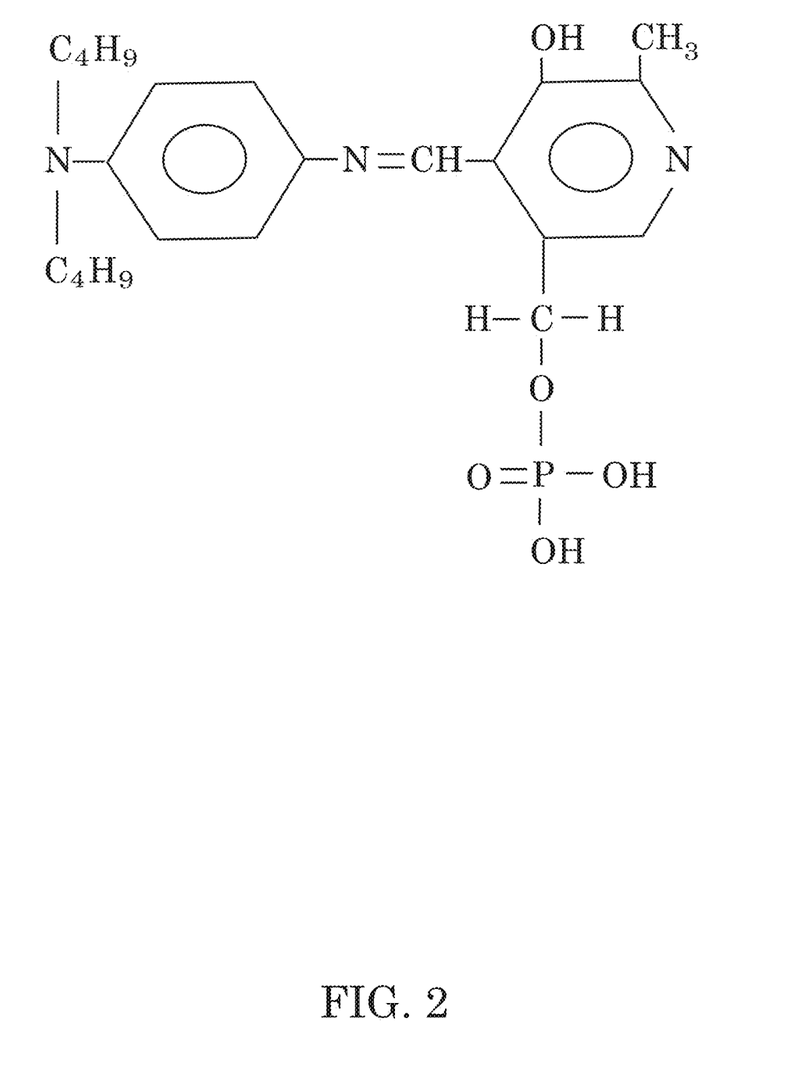
FIG. 2 depicts an embodiment of the chemical structure of N,N-dibutyl-p-phenylenediamine conjugated to pyridoxial 5'phosphate.

The chromophore produced may be a product of reaction between the $H_2S$ products of the enzymatic reaction 102 and a chromogenic agent. A chromogenic agent may be any compound capable of performing a reaction resulting in a chromophore product. For example, in the chromophore producing reaction 103, an $H_2S$-specific chromogenic agent may be used to react with the $H_2S$ product of the enzymatic reaction 102. In one embodiment, the $H_2S$-specific chromogenic agent is a Schiff-Base formed by conjugating N,N-dibutyl-p-phenyldiamine (DBPDA) to pyrodoxal-5-phosphate (PLP), forming N,N-dibutyl-p-phenyldiamine-pyrodoxal-5-phosphate (DBPDA-PLP). The structure of DBPDA-PLP is depicted in FIG. 2.

Figure 3:
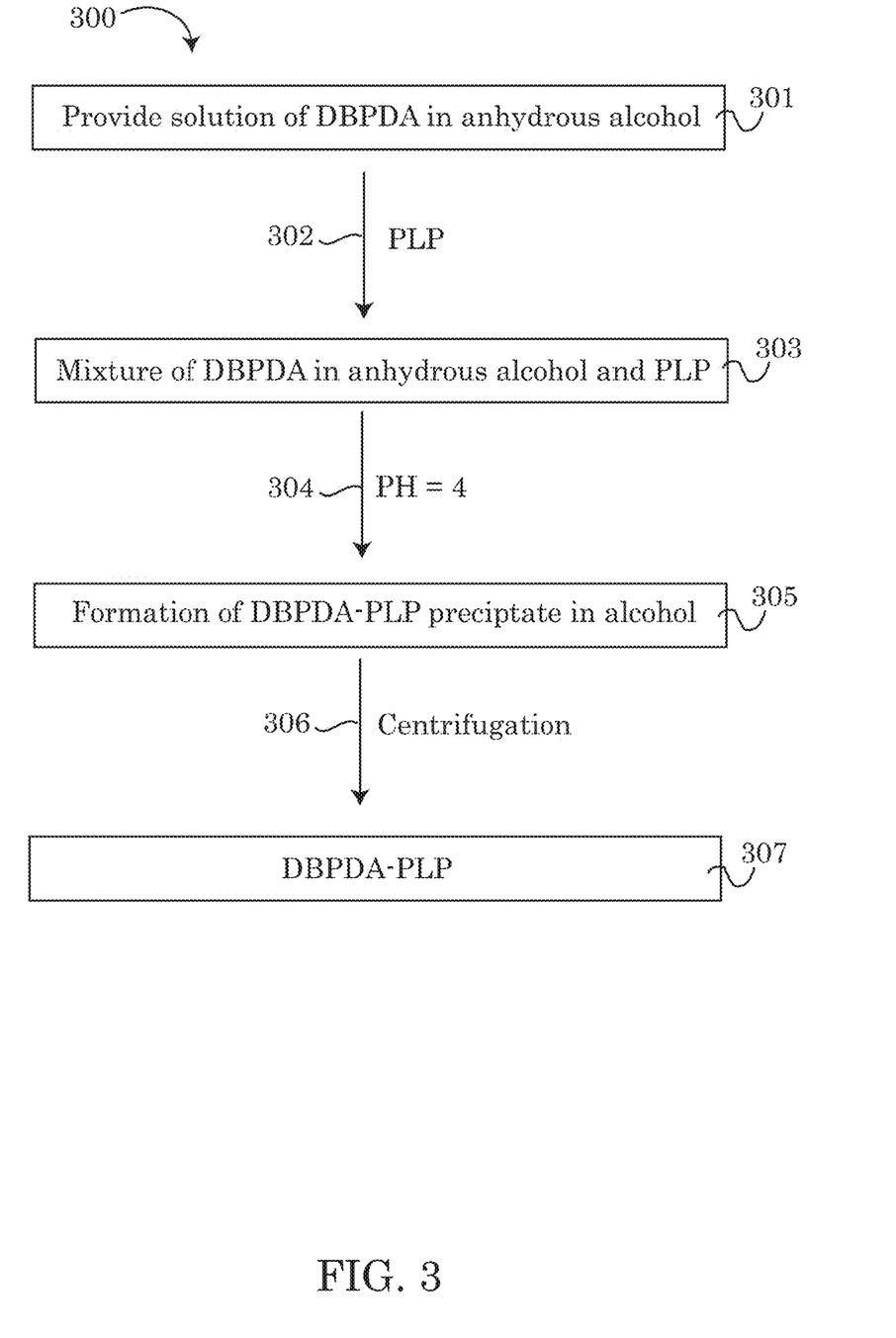
FIG. 3 depicts a flowchart describing an embodiment of a method steps for conjugating N,N-dibutyl-p-phenylenediamine to pyridoxial 5'phosphate.

The chromogenic agent, N,N-dibutyl-p-phenyldiamine-pyrodoxal-5-phosphate (DBPDA-PLP), may be formed in accordance with the embodiment 300 depicted in FIG. 3. In this embodiment, the chromogenic agent is prepared by first providing a solution of DBPDA and anhydrous alcohol 301. The anhydrous alcohol may be any anhydrous C1-C10 alcohol such as anhydrous methanol, ethanol, isopropyl alcohol, butyl alcohol, pentanol, allyl alcohol, geraniol, propargyl alcohol, or any other known anhydrous alcohols.

In one embodiment, the DBPDA in the anhydrous alcohol may be mixed with a solution of PLP 303. The pH of the mixture 303 is adjusted 304 to acidic conditions, between approximately a pH of 3.0-5.0, causing the formation of a DBPDA-PLP precipitate 305. In the exemplary embodiment, the pH may be adjusted to approximately 4.0. The precipitate may be collected by any known method of collection 306 or liquid separation. For example, the precipitate may be collected using a process such as centrifugation 306 or filtration. Once separated from the mixture, the collected precipitate of DBPDA-PLP may be further purified by suspending the precipitate in acidic water followed by a second collection round, performed using centrifugation or filtration. The collected DBPDA-PLP may further be dried under a vacuum over $P_2O_5$.

An embodiment of the method of preparing DBPDA-PLP described above may include providing 300 mg of DBPDA (1.056 mmol) in 10 ml solution of anhydrous ethyl alcohol. The DPBDA solution may be mixed with a 20 ml of PLP (336 mg, 1.26 mmol). The pH of the mixture may be subsequently adjusted to approximately 4.0 to precipitate the DBPDA-PLP conjugate product. The precipitate DBPDA-PLP may be collected using centrifugation. Following the collection of the DBPDA-PLP precipitate, the DBPDA-PLP may be washed and suspended with acidic water having a pH of approximately 4.5. The suspension may be centrifuged a second time and the DBPDA-PLP product may be dried under vacuum over $P_2O_5$.

Figure 4:
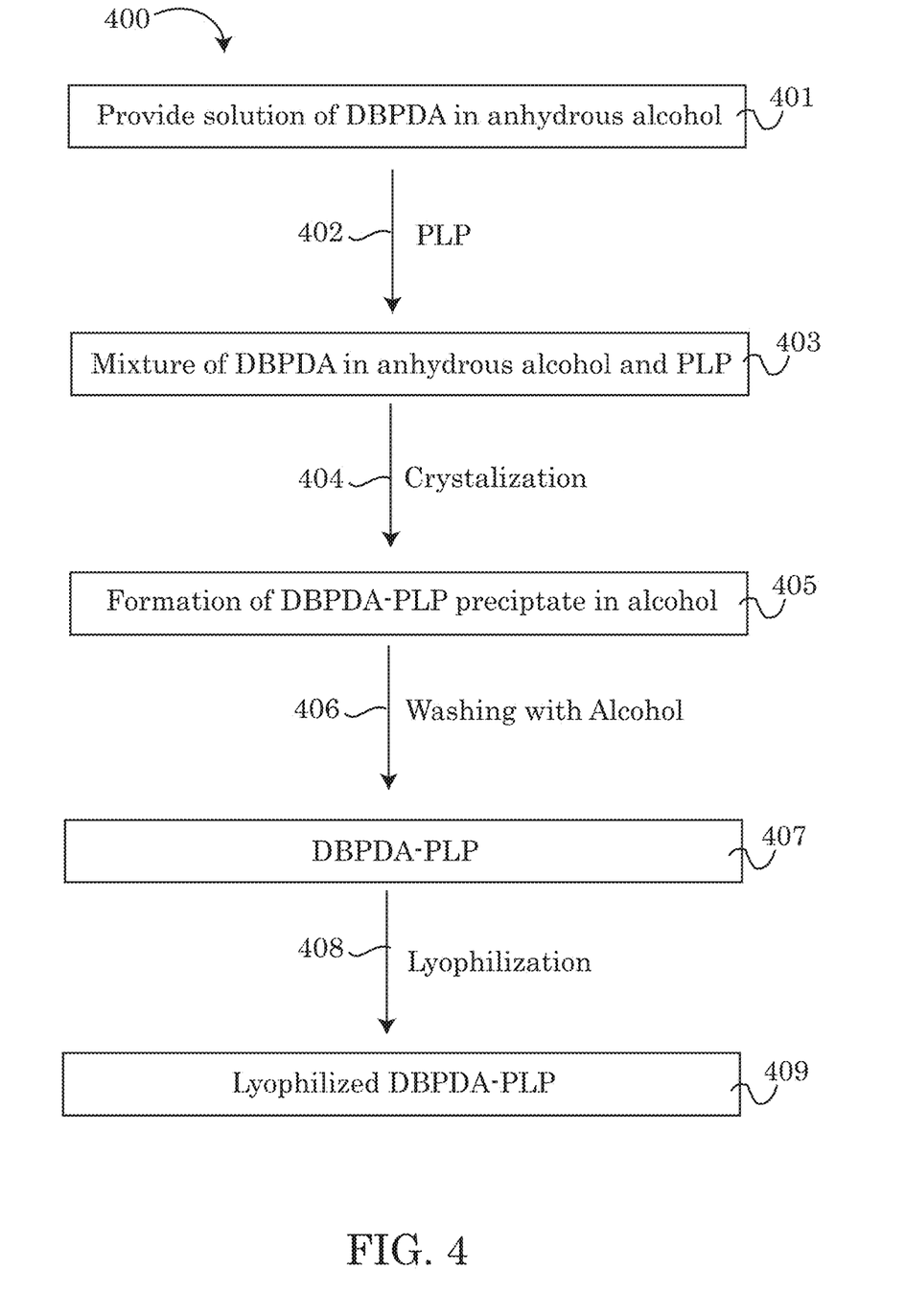
FIG. 4 depicts a flowchart of an embodiment of an alternative method for conjugating N,N-dibutyl-p-phenylenediamine to pyridoxial 5'phosphate.

In an alternative embodiment 400, depicted in FIG. 4, DBPDA-PLP may be prepared by a method including a crystallization step. In this alternative embodiment 400, the first and second step may be similar to the embodiment 300 described above, wherein a solution of DBPDA in anhydrous alcohol may be provided 401. DBPDA in anhydrous alcohol may be mixed with a PLP solution 403. The mixture of DBPDA may be crystallized 404 by cooling the mixture to approximately 0-20° C. In an exemplary embodiment, the mixture 403 may be cooled to approximately 20° C. Once the mixture is cooled, it may be allowed to sit until crystals form. Crystallization may be completed within approximately 48 hours. The crystals of DBPDA-PLP 405 may then be collected in some embodiments. Alternatively, the collected crystals of DBPDA-PLP may be washed with cooled alcohol and then lyophilized.

The alternative embodiment 400 for preparing DBPDA-PLP may be prepared by way of example, by providing 300 mg (1.056 mmol) of DBPDA in 6 ml of anhydrous ethyl alcohol mixed with 20 ml of a PLP solution (336 mg, 1.26 mmol). The DBPDA, PLP, mixture may be cooled to approximately 20° C. and allowed to crystallize. Crystals of DBPDA-PLP may be collected after approximately 48 hours. Once collected, the DBPDA-PLP crystals may be washed with a cooled 75% ethyl alcohol and lyophilized according to known lyophilization methods.

Still other embodiments of the chromophore-producing reaction 103 may further include an oxidant. The oxidant agent may include any Fe(III) containing compound. Examples of an oxidant agent containing Fe(III) may include ferric chloride ($FeCl_3$), potassium ferricyanide ($K_3Fe(CN)_6$), ferric oxide ($Fe_2O_3$), ferric fluoride ($FeF_3$), ferric bromide ($FeBr_3$), and ferric iodide ($FeI_3$). In some embodiments, the oxidant agent may be formulated with a strong acid in the chromophore-producing reaction 103. Any strong acid may be used with the oxidant agent. Examples of a strong acid include HI, HBr, $HClO_4$, HCl, $HClO_3$, $H_2SO_4$ and $HNO_3$.

The resulting product of the chromophore-producing reaction 103 described above is a chromophore. A chromophore may be any chemical group of a compound capable of selective light absorption. Chromophores may result in the coloration of the compound. It is the chromophore's selective light absorption and color properties that may allow for the measurement of the compound's chromophore content. The chromophore's emittance, absorbance, and optical density may be measured to determine the chromophore's concentration following the completion of the chromophore producing reaction 103. In one embodiment, the chromophore concentration may be measured using a spectrophotometer. The measuring step 104 may include generating a standard curve of known concentrations of tHCY. The known concentrations of each point in the standard curve may be determined by any known method such as HPLC. The known concentrations or calibrators' absorbance or fluorescence may be measured at OD 660 or Ex 660/EM700 nm, in one embodiment, to generate the standard curve. Following the generation of the standard curve, the chromophore concentration may also be measured by reading chromophore's absorbance at approximately OD 660 or fluorescence at Ex 660/Em 700 nm, and the tHCY concentration can be determined using a standard curve. In an alternative embodiment, the chromophore's concentration may be measured by fluorescence at a specific excitation wavelength. In the exemplary embodiment, the excitation wavelength may be approximately 660 nm. In yet another alternative embodiment, the chromophore may also have its fluorescence measured at a specific emission wavelength. In the exemplary embodiment, the chromophore's concentration may be measured at an emission wavelength between approximately 700-710 nm.

Embodiments of the tHCY assay 100 may be performed using two reagents in two contemporaneous steps. In this two-step embodiment, the tHCY of the biological fluid may first be reacted with a first reagent (Reagent I). Reagent I may be a combination of a reducing agent, a homocysteinase enzyme and a chromogenic agent. Reagent I in some embodiments may include DTT as the reducing agent, rHCYase as the homocysteinase enzyme and DBPDA-PLP as the chromogenic agent. In this embodiment of the tHCY assay, when the first reagent is combined with the biological fluid, the reducing agent may reduce the disulfide bonds of homocysteine to sulfhydryl bonds. Accordingly, the homocysteinase enzyme may begin reacting with the reduced homocysteine to produce $H_2S$ through the enzymatic reaction described above and may include side products such as ammonia and α-ketobutyrate. The resulting $H_2S$ subsequently binds to the chromogenic agent, such as DBPDA, released from DBPDA-PLP, producing a pre-chromophore.

Once the pre-chromophore has been produced as the product of the plurality of reactions between Reagent I and the biological fluid, a second reagent (Reagent II) may be added to the resulting pre-chromophore. In the exemplary embodiment, the amount of time it takes for Reagent I to completely react with the biological fluid to produce a pre-chromophore may be in as little as approximately five minutes. Subsequent to the formation of the pre-chromophore, the second step of the tHCY assay may include combining the second reagent with the pre-chromophore to produce a chromophore. Reagent II may be any oxidant capable of oxidizing the pre-chromophore into a chromophore. In some embodiments, Reagent II may be an Fe(III) containing compound. For example, the oxidant may be ferric chloride ($FeCl_3$), potassium ferricyanide ($K_3Fe(CN)_6$), ferric oxide ($Fe_2O_3$), ferric fluoride ($FeF_3$), ferric bromide ($FeBr_3$), or ferric iodide ($FeI_3$). Reagent II may also include a strong acid solvent such as HI, HBr, $HClO_4$, HCl, $HClO_3$, $H_2SO_4$ or $HNO_3$. The resulting chromophore may be measured using a photo spectrometer or fluorescence reader, as previously described.

Table I below provides an example of the differences between the assay of the two-reagent embodiment for measuring tHCY compared with a method that utilizes four reagents to calculate tHCY. As shown in the comparison in table 1, the two-reagent assay may significantly benefit from the inclusion of the chromogenic agent, DBPDA-PLP over the unconjugated DBPDA of the four-reagent tHCY assay. DBPDA in the four reagent assay may not be compatible with rHCYase, thus the four-reagent assay requires each reagent to be supplied separately. The two-reagent embodiment, however, realizes an unexpected advantage from using the conjugated DBPDA-PLP as opposed to DBPDA alone. DBPDA-PLP is stable and compatible with rHCYase which allows the chromogenic agent, homocysteinase enzyme, and the reducing agent to be combined into a single reagent, as opposed to the embodiment that separates the components individually.

TABLE 1

Differences between two reagent and four reagent tHCY assays

| Item | Two-Reagent tHCY Assay | Four-Reagent tHCY Assay |
|---|---|---|
| Reagent | Reagent I: a combination of DTT, rHCYase and DBPDA-PLP. Reagent II: $FeCl_3$ | Reagent I: DTT Reagent II: rHYCase Reagent III: DBPDA Reagent IV: $K_3Fe(CN)_6$ |
| Protocols | Step 1: Reduction reaction, enzymatic reaction, and pre-chromophore reaction. Step 2: Chromophore reaction | Step 1: Reductive reaction. Step 2: Enzymatic reaction. Step 3: Pre-chromophore reaction. Step 4: Chromophore Reaction |

Embodiments of the tHCY assays described herein may be performed manually by a person at each step or using an automated analyzer. The automated analyzer may determine the characteristics of the biological fluid samples quickly according to the protocol of the assay with minimal human interaction. In the exemplary embodiment, the tHCY assay may be performed using a Hitachi 912 automatic analyzer; however, alternative embodiments may be performed using any automated analyzer available or preferred by the user. In an embodiment using a Hitachi 912 automatic analyzer, the tHCY assay may have a throughput of approximately 360 tests per hour and a linear detection range between approximately 3.7-47.1 μmol/L.

Figure 6:
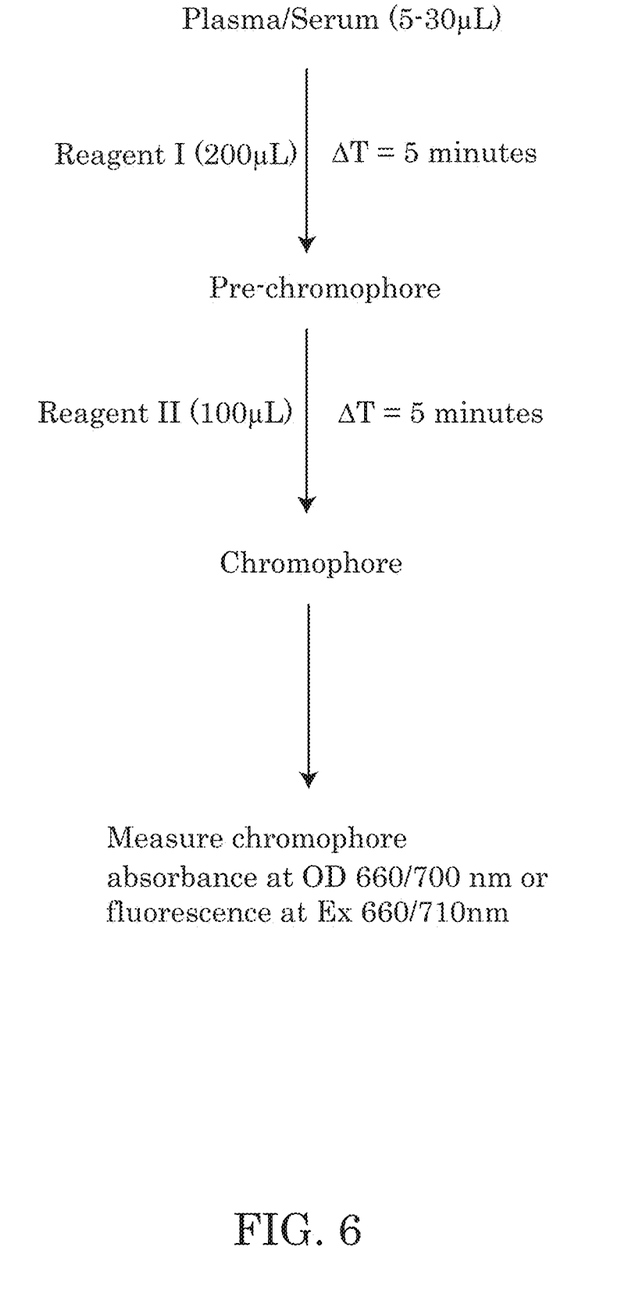
FIG. 6 depicts a flow chart of the protocol of an embodiment of a two reagent tHCY assay.

Referring to FIG. 6, which depicts a flow chart of an embodiment of the tHCY assay described in table 1 above, the biological fluid such as serum or plasma may be combined with Reagent I. In the embodiment described in FIG. 6, approximately 200 μL of Reagent I may be combined with approximately 30 μL of serum or plasma to form the pre-chromophore. As described in the embodiment of FIG. 6, the amount of time (ΔT) for the reaction between the plasma or serum and Reagent I to complete may be approximately 5 minutes. Following the production of the pre-chromophore, 100 μL of Reagent II may be added to the pre-chromophore. This second reaction between Reagent II and the pre-chromophore may occur within approximately 5 minutes, resulting in the formation of a chromophore capable of having its absorbance or fluorescence measured by a spectrophotometer or a fluorescence reader. In the particular embodiment depicted in FIG. 6, the chromophore may have its absorbance measured at a primary wavelength of approximately 660 nm and/or a secondary wavelength of approximately 700 nm. Embodiments of this assay may be performed between room temperature and 37° C. While the embodiment in FIG. 6 discloses a sample volume of 30 μl, the sample volume may vary depending on the method of measuring the chromophore. For example, in an embodiment measuring absorbance via the measurement of a fluorescence excitation or emission wavelength, a smaller sample volume as little as approximately 5 μm may be used.

Embodiments of the two-reagent tHCY assay may also be provided as a kit comprising all reagents to perform the assay. Embodiments of the two-reagent assay kit may include one or more of the following components: a first reagent (Reagent I), a second reagent (Reagent II), a first buffer (buffer I) and a second buffer (buffer II). Alternative embodiments may further include calibrators and controls.

As described previously, Reagent I may include a reduction agent, a homocysteinase enzyme, and a chromogenic agent. Embodiments of Reagent II may include one or more oxidants, such as any of the Fe(III) containing compounds previously described. In some embodiments, a first buffer may be used to maintain the pH of the mixture of Reagent I. Buffer I may be any biological buffer capable of maintaining pH of the mixture in the range of approximately 7.5-8.5. One example of a buffer that may be used is a sodium phosphate or potassium phosphate buffer. In addition to phosphate buffers, other buffer I solutions may include 3-{[tris(hydroxymethyl)methyl] amino}propanesulfonic acid (TAPS), 3-[N-tris(hydroxymethyl)methylamino]-2-hydroxypropanesulfonic acid (TAPSO), N,N-bis(2-hydroxyethyl)glycine(bicine), tris(hydroxymethyl)methylamine(tris), N-tris(hydroxymethyl)methylglycine(tricine), 4-2-hydroxyethyl-1-piperazineethanesulfonic acid (HEPES), 2-{[tris(hydroxymethyl)methyl]amino}ethanesulfonic acid (TES), 3-(N-morpholino)propanesulfonic acid (MOPS), piperazine-N, N'-bis(2-ethanesulfonic acid) (PIPES), succinic acid, saline sodium citrate and borate saline buffers. In one or more embodiments, buffer I may be added to Reagent I. Buffer I may be added prior to mixing Reagent I with the biological sample to dilute Reagent I to a desired concentration.

In an alternative embodiment, Buffer I may further include a nonionic surfactant. A nonionic surfactant may include one or more of the following compounds: cetomacrogol 1000, cetostearyl alcohol, cetyl alcohol. cocamide DEA, cocamide MEA, decyl glucoside, IGEPAL CA-630, isoceteth-20, lauryl glucoside, monolaurin, a narrow range ethoxylate, nonidet P-40, nonoxynols such as nonoxynol-9, NP-40, octaethylene glycol monododecyl ether, N-octyl beta-D-thioglucopyranoside, octyl glucoside, oleyl alcohol, pentaethylene glycol monododecyl ether, poloxamer 407, polyglycerol polyricinoleate, polysorbate, polysorbate 20, polysorbate 80, sorbitan monostearate, sorbitan tristearate, stearyl alcohol, triton x-100, tween-80, and a combination of surfactants thereof. Alternative embodiments of the tHCY assay kit may include buffer II either separately or premixed with Reagent II. Buffer II may be any strong acid, including HI, HBr, $HClO_4$, HCl, $HClO_3$, $H_2SO_4$ and $HNO_3$.

Embodiments of the tHCY assay may further comprise a set of one or more calibrators and/or a set of one or more controls. The calibrators and/or controls may each include one or more samples of matrix plasma containing tHCY of a known concentration. The calibrator may be used as a reference material to calibrate or standardize the instrument measuring the concentration of tHCY, such as the spectrophotometer. The controls having a known concentration may be plotted along the standard curve generated by the calibrators and may be used to compare with the spectrophotometer readings of the chromophore measurements resulting from the assay procedure. For the more accurate measurements, the calibration curve may be measured once per day. The controls, on the other hand, may be measured with each set of samples that are measured using the assay. In the preferred embodiment, if control values are within ±10% of the pre-calculated concentrations, then the assay may be considered valid. Table 2 below provides an example of parameters that may be used for an embodiment of the tHCY assay performed using an automatic analyzer.

TABLE 2

Parameters of the Two-Reagent tHCY Assay performed on the Hitachi 912 Automatic Analyzer

| | Sample | | Reagent | | |
| --- | --- | --- | --- | --- | --- |
| Step | Sample | Volume (µl) | Reagent | Volume (µl) | Time (minutes) |
| Step 1 | Calibrators | 30 | I | 200 | 5 |
| | Controls | 30 | I | 200 | |
| | Sample | 30 | I | 200 | |
| Step 2 | | | II | 100 | 5 |
| End-point read | Wavelength ($2^{nd}$/primary) | One end point | Calibration type | Analyze cycle (sec) | Total assay (min) |
| | 700 nm/ 660 nm | 30 | | Linear | 10 | 10 |

In the embodiment provided in Table 3 and Table 4 below, three calibrators and two controls are provided. The calibrators may include tHCY concentrations of approximately 4 µmol/L, 15 µmol/L, and 44 µmol/L. The controls in the embodiments may have a known concentration such as 8 µmol/L and 24 µmol/L or any other known concentration that may reside along the standard curve generated by the calibrators. Although the exemplary embodiments may include three calibrators and two controls, the number of controls and calibrators may vary. Likewise, the concentrations of the calibrators and controls may also vary at any interval ≥ approximately 3.5 µmol/L.

TABLE 3

Kit Contents for 100 Samples and Stabilities of Reagents Before Reconstitution

| Reagent | Components | Quantity | Stability 25° C. | 4° C. | −25° C. |
| --- | --- | --- | --- | --- | --- |
| Reagent I | DTT rHCYase DBPDA-PLP | 9.0 mg 0.3 mg 36 mg | 24 hours | 1 month | 1 year |
| Reagent II | 64 mM $FeCl_3$ in 1.2N HCL | 15 ml | - 6 months | 2 years | — |
| Buffer I | Sodium phosphate buffer (pH 8.3) containing Triton X-100 | 40 ml | 6 months | 2 years | — |
| Calibrators | Matrix Plasma containing 4, 15 and 44 µmol/L, respectively. | 0.5 ml each | 12 hours | 1 month | 2 years |
| Controls | Matrix Plasma containing 8 and 24 µmol/L, respectively. | 0.5 ml each | 12 hours | 1 month | 2 years |

TABLE 4

Alternative Embodiment of a Kit for 100 Samples and Stabilities of Reagents for the Two-Reagent tHCY Assay

| Reagent | Components | Quantity | Stability 25° C. | 4° C. | −20° C. |
| --- | --- | --- | --- | --- | --- |
| Reagent I | DTT rHCYase DBPDA-PLP | 20 mg 0.2 mg 60 mg | 24 hours | 1 month | 1 year |
| Reagent II | $K_3Fe(CN)_6$ | 8 mg | 6 months | 2 years | — |
| Buffer I | Sodium phosphate buffer (pH 8.3) containing Triton X-100 | 40 ml | 6 months | 2 years | — |
| Buffer II | 1.5N $H_2SO_4$ | 10 ml | 2 years | — | — |
| Calibrators | Matrix plasma containing 4, 15 and 44 µmol/L, respectively. | 0.5 ml each | 24 hours | 4 weeks | 2 years |
| Controls | Matrix plasma containing 8 and 24 µmol/L, respectively. | 0.5 ml each | 24 hours | 4 weeks | 2 years |

In embodiments of the tHCY kit including calibrators and controls, the calibrators and controls may be prepared by spiking L-homocysteine in the plasma matrix. In one embodiment, the tHCY assay kit may be comprised of three calibrators and two controls. The quantity of each reagent, buffer, calibrator and control may vary in each embodiment. For example, in Tables 2 and 3 above, the quantities provided are able to test the tHCY of 100 biological samples. The number of samples that may be tested may vary depending on the variations of quantities. Furthermore, the quantities and ratios of each component in the kit may vary as the components of the kits vary from kit to kit.

One embodiment of a method for preparing the calibrators and controls, may be performed by preparing a stock solution of L-Homocysteine ($[L-HCY]_2$) of a known concentration, by dissolving the $[L-HCY]_2$ in the solution. The stock solution may be vortexed for up to 24 hours at room temperature. The stock solution may then be diluted using known methods, such as serial dilution using any known buffer solution. In the exemplary embodiment, phosphate buffered saline (PBS) may be used. Multiple working solutions of varying concentrations may be prepared from the stock solution. For example, 25, 50, 100 and 200 µmol/L working solutions may be prepared respectively. The standard calibrators (S-1, S-2 and S-3) and controls (C-L, C-H) may be prepared by spiking different concentrations of the $[L-HCY]_2$ working solutions into the plasma matrix. Embodiments of this procedure may spike the plasma matrix in a volume ratio of 1:10. After spiking the plasma matrix, the concentrations of the standards may be determined using HPLC methods. Table 5 provides one example of an embodiment for preparing the standard calibrators and controls.

TABLE 5

Preparation of Standards

| Standards | Plasma matrix volume (ml) | Spiking solution Concentration of $[L-HCY]_2$ (µmol/L) | Volume (ml) | Values of L-HCY(µmol/L) determined by HPLC |
|---|---|---|---|---|
| S-1 | 90 | 0 | 10 | 3.2 |
| S-2 | 90 | 50 | 10 | 15.6 |
| S-3 | 90 | 200 | 10 | 43.8 |
| C-L | 90 | 25 | 10 | 7.8 |
| C-H | 90 | 100 | 10 | 25.4 |

Embodiments of the invention may utilize concentrations of the calibrators and controls in the two-reagent tHCY assay determined using any known HPLC method. In one embodiment of an HPLC method, a 100 µl plasma and internal recovery standard of 1.1 mol/L N-acetylcysteine (NAC) may be used. Ten µl of the plasma/standard may be treated with 10 µl of 10% tri-n-butylphosphate (TBP) in dimethylformamide at 4° C. for 60 minutes. The reaction mixture may then be precipitated with 100 µl of 10% trichloroacetic acid containing 1 mmol/L EDTA. The precipitated reaction mixture may be centrifugated at approximately 13,000 rpm for approximately 3 minutes. The resulting 100 µl supernatant may be collected into a new test tube. Following the collection of the supernatant, 250 µl of a 0.125 mol/L borate buffer (pH 9.2) containing 4 mmol/L EDTA, 20 µl of 1.5N sodium hydroxide and 100 µl of 1 mg/ml 4-fluoro-7-sulfobenofurazan ammonium salt solution may be added to the test tube. Following the mixture of the supernatant and the borate buffer, the tube may be mixed and incubated at approximately 60° C. for approximately 1 hour, followed by cooling the mixture to room temperature. The mixture may be filtered through a 0.22 µm filter, collecting the sample left behind.

The filtered sample may be run through any HPLC device, such as a Hitachi L-6200 A Intelligent Pump HPLC or an equivalent thereof. In this example of an embodiment, 20 µl of the filtered sample may be loaded on a reverse-phase Supelcosil LC-18-DB column, having a particle size of 5 µm and dimensions of 25 cm×4.8 mmol/L. The filtered sample may be placed in the HPLC and run at room temperature. Elution may occur isocratically using a phosphate buffer (such as potassium phosphate at a pH of 3.5). The phosphate buffer may contain 3.5% acetonitrile and enter the HPLC at a flow rate of approximately 2.0 ml/min., resulting in approximate retention times for eluting from the column as follows: cysteine 3.6 min.; homocysteine 4.2 min.; and NAC 14.1 min.

In the embodiment of the HPLC method described above, $[L-HCY]_2$ at concentrations of 5, 25 and 50 µmol/L may be equal to L-HCY concentrations of 10, 50 and 100 µmol/L, respectively, the L-HCY values of the calibrators and controls may be calculated in triplicate. The results of this preparation embodiment are recorded in Table 5 below.

TABLE 5

Determination of Standard Values

| Samples | S-1 | S-2 | S-3 | C-L | C-H |
|---|---|---|---|---|---|
| HPLC area ($\times 10^3$) | 9.73 | 45.6 | 132.4 | 23.8 | 74.9 |
|  | 9.67 | 47.8 | 128.9 | 23.7 | 77.6 |
|  | 9.2 | 46.1 | 130.3 | 22.5 | 74.6 |
| Average | 9.5 | 46.5 | 130.5 | 23.2 | 75.7 |
| SD | 0.29 | 1.17 | 0.83 | 1.69 | 1.76 |
| CV % | 3.0 | 3.6 | 2.5 | 2.2 | 1.35 |
| L-HCY (µmol/L) | 3.2 | 7.8 | 15.6 | 25.4 | 43.8 |

The precision of the tHCY assay described above was evaluated in a study based on the NCCLS EP5-T2 guidelines entitled "Evaluation of Precision Performance of Clinical Chemistry Devices." In this study, the tHCY assay precisions were determined after analyzing three plasma samples containing a low, medium and high concentration of tHCY. These three samples were tested in parallel assays. Precision was measured within an assay (within-assay precision) and between assays (between-assay precision). To measure the within-assay precision, results from 10 parallel analytical setups were determined, whereas the between-between-assay precision calculated assay results in 10 successive assays, carried out over 10 assays. The results of the precision tests are described in Table 6 below.

TABLE 6

Precision of the Two-Reagent tHCY Assay

| Assay | Sample 1 | Sample 2 | Sample 3 |
|---|---|---|---|
| a. Within-assay precision | | | |
| Average tHCY (µmol/L) | 9.0 | 14.0 | 45.1 |
| SD | 0.38 | 0.23 | 0.84 |
| CV (%) | 4.2 | 1.6 | 1.9 |
| b. Between-assay precision | | | |
| Average tHCY (µmol/L) | 9.2 | 14.6 | 47.1 |
| SD | 0.86 | 0.93 | 1.36 |
| CV (%) | 9.3 | 6.3 | 2.9 |

Figure 7:
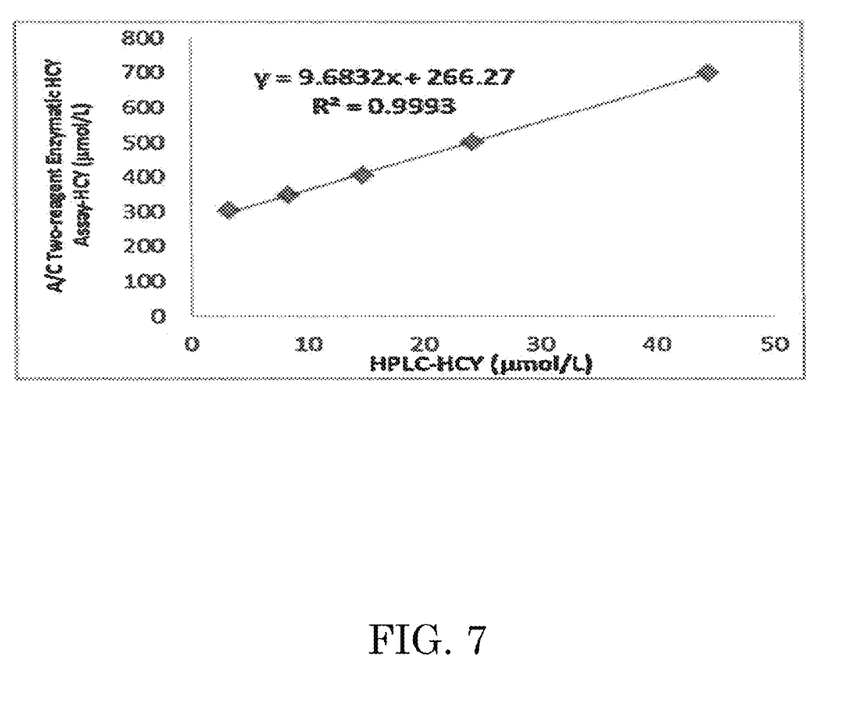
FIG. 7 depicts a graphical representation of the linearity of an embodiment of the tHCY assay.

To determine the linearity of the tHCY assay, ten tests for five plasma samples containing varying concentrations of L-HCY, between 3.2-44.6 μmol/L were measured by the tHCY assay using a Hitachi 912 automatic analyzer and with HPLC. The results of the linearity tests are depicted in Table 7 below and in FIG. 7.

TABLE 7

Linearity of the Two-Reagent tHCY Assay

| HPLC | HCY (μmo/L) | 3.2 | 8.4 | 14.8 | 24.2 | 44.6 |
|---|---|---|---|---|---|---|
| tHCY Assay | OD660/700 nm | 302 | 348 | 403 | 501 | 700 |

The recovery rate of the tHCY assay was determined on the Hitachi 912 automatic analyzer over the entire dynamic range of concentrations measurable by the analyzer. To measure the recovery rate, one sample of tHCY, with a concentration of 50 μmo/L, was serially diluted 2, 4, and 8 times with the phosphate buffer saline (PBS). The samples were analyzed using 10 replicates per a single run. The dilution recovery rates and the average values were calculated. Table 8 below provides the results of the recovery rate analysis. As it can be seen below, the recovery rate of the tHCY assay, compared with the theoretical concentrations, was over 98%.

TABLE 8

Recovery Rate of the Two-Reagent tHCY Assay

| Dilution | Theoretical tHCY (μmo/L) | Observed tHCY (μmo/L) | Recovery Rate (%) |
|---|---|---|---|
| Undiluted | 50 | 49.9 | 100 |
| 2 | 25 | 25.3 | 98.8 |
| 4 | 12.5 | 12.7 | 98.4 |
| 8 | 6.25 | 6.3 | 99.2 |

In an effort to determine the detection limit of the quantification capabilities of the tHCY assay on the Hitachi 912 automatic analyzer, the limit of quantification was defined as the lowest concentration having a CV<20%. A sample of 7.4 μmo/L tHCY was diluted with PBS to a concentration of 3.7 μmo/L. The tHCY assay was performed using 20 replicates and the average of all twenty samples is provided in Table 9 below. The results demonstrate that the minimal limit of quantification of the tHCY assay using the Hitachi automatic analyzer is approximately 3.7 μmo/L.

TABLE 9

Detection Limit of the Two-Reagent tHCY Assay
Using the Hitachi 912 Automatic Analyzer
HCY (μmo/L)

| Exp-1 | 4.3 | Exp-11 | 3.4 |
|---|---|---|---|
| Exp-2 | 4 | Exp-12 | 3.5 |
| Exp-3 | 4 | Exp-13 | 3.5 |
| Exp-4 | 3.4 | Exp-14 | 3.7 |
| Exp-5 | 4.1 | Exp-15 | 3.4 |
| Exp-6 | 4.4 | Exp-16 | 3.7 |
| Exp-7 | 3.7 | Exp-17 | 3.4 |
| Exp-8 | 3.5 | Exp-18 | 3.7 |
| Exp-9 | 3.8 | Exp-19 | 3.2 |
| Exp-10 | 3.7 | Exp-20 | 3.2 |
| Average | | 3.7 | |
| SD | | 0.34 | |
| CV (%) | | 9.2 | |

Figure 5:
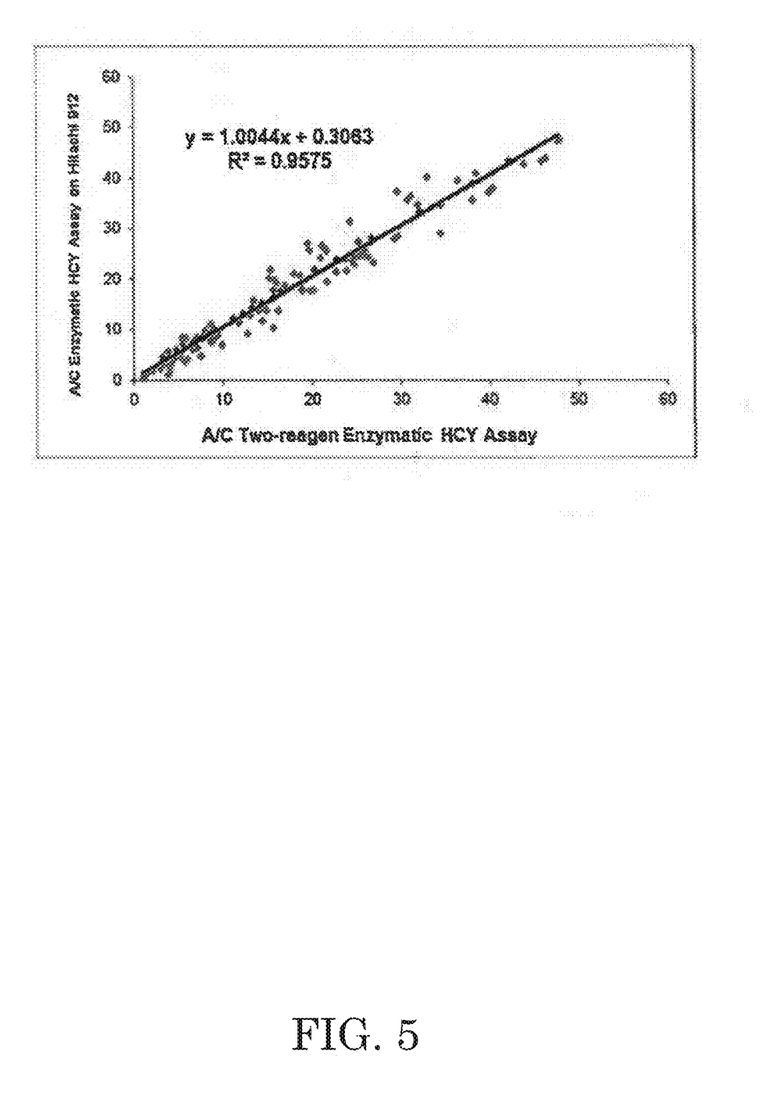
FIG. 5 depicts a graphical representation comparing results of an embodiment of a two reagent total homocysteine assay and a total homocysteine assay that utilizes four reagents.
Figure 8:
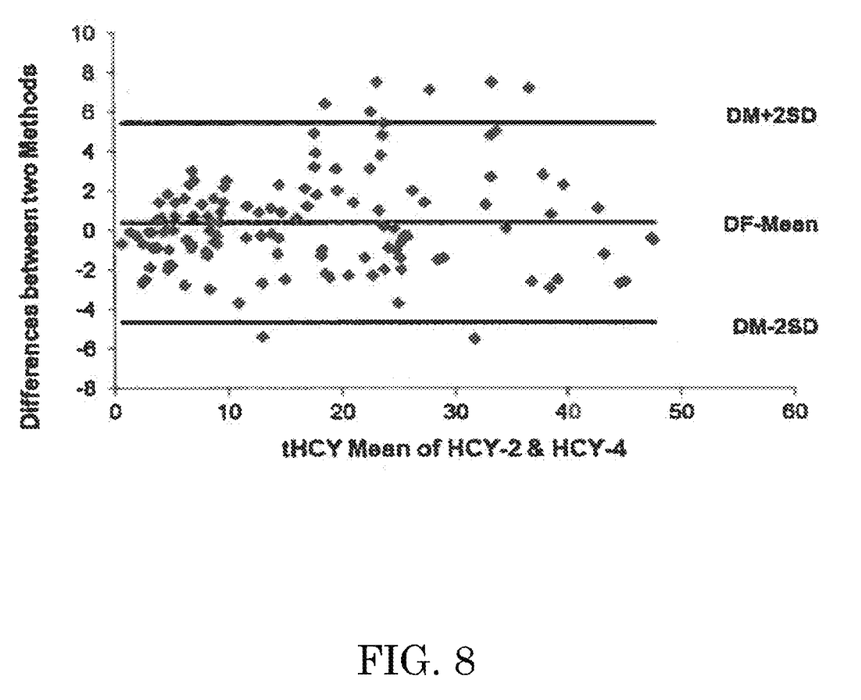
FIG. 8 depicts a graphical representation of a Bland Altman analysis comparing the accuracy of a two reagent embodiment of the tHCY assay compared with a four reagent assay, within ±2 standard deviations.

An assessment was performed to compare the accuracy of the embodiment of the tHCY assay using two reagents (HCY-2) to determine tHCY concentration with other methods, that use four reagents (HCY-4). To perform the accuracy assessment, one-hundred and twenty-five samples were measured using the HCY-2 assay described herein and a HCY-4 assay. Both assays were analyzed using a Hitachi 912 automatic analyzer. The results of the accuracy assessment are provided in Table 10 below. The results in Table 10 are subsequently plotted graphically in a correlation analysis depicted in FIG. 5 and a Bland-Altman analysis depicted in FIG. 8. A linear regression of the results depicted in FIG. 5, with the correlation coefficient of $R^2=0.96$, yielded y=1.00+ 0.30 wherein the slope is 1.0. Based on the results in Table 10a, 10b, FIGS. 5 and 8, it can be concluded that the two reagent assay is capable of determining tHCY concentration as accurately as or better than the HCY-4 assay.

TABLE 10a

Accuracy of the Two Reagent tHCY Assay, Samples 1-64

| Sample ID# | HCY (μmol/L) | | |
|---|---|---|---|
| | HCY-4 | HCY-2 | DF |
| 1 | 7.5 | 8.8 | −1.3 |
| 2 | 24.7 | 24.6 | 0.1 |
| 3 | 1.1 | 3.8 | −2.7 |
| 4 | 8.5 | 9.1 | −0.6 |
| 5 | 15.2 | 14.3 | 0.9 |
| 6 | 27.3 | 25.3 | 2 |
| 7 | 47.2 | 47.6 | −0.4 |
| 8 | 17.8 | 18.8 | −1 |
| 9 | 22.8 | 24.8 | −2 |
| 10 | 43.2 | 42.1 | 1.1 |
| 11 | 24.3 | 26.3 | −2 |
| 12 | 21.4 | 22.6 | −1.4 |
| 13 | 34.6 | 34.5 | 0.1 |
| 14 | 37.9 | 40.4 | −2.5 |
| 15 | 17.8 | 20.2 | −2.4 |
| 16 | 38.9 | 38.1 | 0.8 |
| 17 | 28.3 | 29.7 | −1.4 |
| 18 | 2.9 | 3.8 | −0.9 |
| 19 | 7.5 | 8.6 | −1.1 |
| 20 | 13.7 | 14.9 | −1.2 |
| 21 | 24.3 | 25.3 | −1 |
| 22 | 47.4 | 47.9 | −0.5 |
| 23 | 17.6 | 18.9 | −1.3 |
| 24 | 24.5 | 25.9 | −1.4 |
| 25 | 42.7 | 43.9 | −1.2 |
| 26 | 25 | 25.6 | −0.6 |
| 27 | 21.8 | 23.9 | −2.3 |
| 28 | 29 | 34.5 | −5.5 |
| 29 | 37 | 39.9 | −2.9 |
| 30 | 19.4 | 21.7 | −2.3 |
| 31 | 35.5 | 38.1 | −2.6 |
| 32 | 27.8 | 29.3 | −1.5 |
| 33 | 3.7 | 5.7 | −2 |
| 34 | 3.9 | 5.7 | −1.8 |
| 35 | 4.6 | 3.2 | 1.4 |
| 36 | 4.4 | 3.8 | 0.6 |
| 37 | 8.4 | 7.1 | 1.3 |
| 38 | 17.8 | 15.7 | 2.1 |
| 39 | 12.3 | 11.1 | 1.2 |
| 40 | 6.3 | 7.2 | −0.9 |
| 41 | 1.8 | 2.1 | −0.3 |
| 42 | 8.5 | 7.8 | 0.7 |
| 43 | 2.9 | 3 | −0.1 |
| 44 | 7.3 | 6.6 | 0.7 |
| 45 | 0.3 | 1 | −0.7 |
| 46 | 6.0 | 3.8 | 1.8 |
| 47 | 13.2 | 12.3 | 0.9 |
| 48 | 16.3 | 15.7 | 0.6 |
| 49 | 7 | 5.4 | 1.6 |
| 50 | 17.5 | 19.7 | −2.2 |
| 51 | 23.8 | 22.8 | 1 |
| 52 | 8.8 | 8.4 | 0.4 |
| 53 | 23.9 | 23.7 | 0.2 |
| 54 | 3.3 | 4.2 | −0.9 |

TABLE 10a-continued

Accuracy of the Two Reagent tHCY Assay, Samples 1-64

| Sample ID# | HCY (μmol/L) | | |
|---|---|---|---|
| | HCY-4 | HCY-2 | DF |
| 55 | 8.7 | 9.4 | -0.7 |
| 56 | 11.7 | 14.4 | -2.7 |
| 57 | 25.3 | 25.6 | -0.3 |
| 58 | 43.8 | 46.4 | -2.6 |
| 59 | 12.8 | 13.1 | -0.3 |
| 60 | 2.1 | 4 | -1.9 |
| 61 | 13.7 | 16.2 | -2.5 |
| 62 | 6.1 | 6.6 | -0.5 |
| 63 | 4.2 | 6 | -1.8 |
| 64 | 6.9 | 9.9 | -3 |

TABLE 10b

Accuracy of the Two Reagent tHCY Assay, Samples 65-125

| Sample ID# | HCY (μmol/L) | | |
|---|---|---|---|
| | HCY-4 | HCY-2 | DF |
| 65 | 1.5 | 4 | -2.5 |
| 66 | 11.4 | 11.8 | -0.4 |
| 67 | 4.2 | 4.3 | -0.1 |
| 68 | 21.7 | 20.3 | 1.4 |
| 69 | 9.1 | 12.8 | -3.7 |
| 70 | 2.2 | 2.9 | -0.7 |
| 71 | 4.8 | 7.6 | -2.8 |
| 72 | 4.3 | 5.3 | -1 |
| 73 | 10.3 | 15.7 | -5.4 |
| 74 | 6.4 | 7.1 | -0.7 |
| 75 | 8.9 | 9.2 | -0.3 |
| 76 | 23.7 | 24.6 | -0.9 |
| 77 | 3.2 | 3.3 | -0.1 |
| 78 | 9.4 | 9 | 0.4 |
| 79 | 14.2 | 14.6 | -0.4 |
| 80 | 23.2 | 26.9 | -3.7 |
| 81 | 43.2 | 45.9 | -2.7 |
| 82 | 17.6 | 16.4 | 1.2 |
| 83 | 25.4 | 21.6 | 3.6 |
| 84 | 40.2 | 33 | 7.2 |
| 85 | 26.1 | 21.3 | 4.6 |
| 86 | 24.1 | 21 | 3.1 |
| 87 | 33.4 | 32.1 | 1.3 |
| 88 | 40.8 | 38.5 | 2.3 |
| 89 | 21.1 | 18 | 3.1 |
| 90 | 36.2 | 31.2 | 5 |
| 91 | 28.3 | 26.7 | 1.4 |
| 92 | 4 | 3.5 | 0.5 |
| 93 | 8.4 | 8.4 | 0 |
| 94 | 13.8 | 14 | -0.2 |
| 95 | 25.7 | 26 | -0.3 |
| 96 | 20.1 | 15.2 | 4.9 |
| 97 | 27 | 19.5 | 7.5 |
| 98 | 20.6 | 18.6 | 2 |
| 99 | 25.7 | 19.7 | 6 |
| 100 | 35.6 | 30.8 | 4.8 |
| 101 | 39.3 | 38.5 | 2.8 |
| 102 | 21.8 | 15.4 | 6.4 |
| 103 | 31.4 | 24.3 | 7.1 |
| 104 | 6.1 | 4.7 | 1.4 |
| 105 | 5.2 | 5.2 | 0 |
| 106 | 5.7 | 5 | 0.7 |
| 107 | 7.6 | 5.5 | 2.3 |
| 108 | 9.8 | 8.9 | 0.9 |
| 109 | 18.7 | 16.9 | 1.8 |
| 110 | 14.3 | 13.2 | 1.1 |
| 111 | 11.1 | 6.6 | 2.5 |
| 112 | 4.4 | 4.4 | 0 |
| 113 | 10.3 | 8.9 | 1.4 |
| 114 | 4.8 | 4.8 | 0 |
| 115 | 9.6 | 8 | 1.6 |
| 116 | 1.3 | 1.4 | -0.1 |
| 117 | 8.4 | 5.4 | 3 |
| 118 | 10.7 | 15.8 | 3.9 |
| 119 | 10.8 | 8.6 | 2.2 |
| 120 | 26.5 | 21.1 | 5.4 |
| 121 | 19.2 | 16 | 3.2 |
| 122 | 15.7 | 13.4 | 2.3 |
| 123 | 8.3 | 5.8 | 2.5 |
| 124 | 37.1 | 29.8 | 7.5 |
| 125 | 34.6 | 31.9 | 2.7 |

To determine the analytical specificity of the tHCY assay, a lipid interference experiment was conducted to study the effects of lipids on the tHCY assay. The lipid interference experiment was performed using a plasma sample having a tHCY concentration of 22.2 μmol/L, spiked with a lipid mixture (1000×) between 0-10×. The samples were each analyzed in duplicate and the interference was calculated using interference formula:

$$\frac{tHCY\ \mu mol/L\ (\text{spiked sample} - \text{non-spiked sample})}{tHCY\ \mu mol/L\ (\text{non-spiked sample})} \times 100 = \%\ \text{interference}$$

The results, provided below in Table 11, demonstrate that with lipid concentrations of up to 10× indicate <5% interference in the two-reagent tHCY assay.

TABLE 11

Lipid Interference in the tHCY Assay

| | | Samples | | | | | |
|---|---|---|---|---|---|---|---|
| | | L0 | L1 | L2 | L3 | L4 | L5 |
| Amount spiked-in lipid (X) | | 0 | 0.6 | 1.25 | 2.5 | 5 | 10 |
| OD 660/ 700 nm | Exp-1 | 20.6 | 22.9 | 22.4 | 22.6 | 21.9 | 21.9 |
| | Exp-2 | 23.4 | 22.6 | 21.4 | 21.9 | 22.9 | 22.4 |
| | Average | 22 | 22.75 | 21.9 | 22.25 | 22.4 | 22.15 |
| | % | 100 | 103.4 | 96.3 | 101.6 | 100.7 | 98.9 |

The analytical specificity of the tHCY assay was further tested to determine the interfering effects of albumin using a method similar to the lipid-interference experiment described above. Similar to the lipid interference, a plasma sample with a known tHCY concentration of 22.2 μmol/L was spiked with albumin. The albumin ranged in concentration between 0-10 mg/ml. The samples were analyzed in duplicate and the interference was calculated. The results, depicted in Table 12 below, demonstrate that albumin concentrations up to 10 mg/ml provide <5% interference in the tHCY assay.

TABLE 12

Albumin Interference in the Two-Reagent_tHCY Assay

| | | Samples | | | | | |
|---|---|---|---|---|---|---|---|
| | | A0 | A1 | A2 | A3 | A4 | A5 |
| Amount of albumin (mg/ml) | | 0 | 0.6 | 1.25 | 2.5 | 5 | 10 |
| OD | Exp-1 | 20.6 | 22.1 | 22.4 | 21.6 | 23.1 | 22.9 |

TABLE 12-continued

Albumin Interference in the Two-Reagent_tHCY Assay

| | | Samples | | | | | |
|---|---|---|---|---|---|---|---|
| | | A0 | A1 | A2 | A3 | A4 | A5 |
| 660/ | Exp-2 | 23.4 | 21.6 | 21.9 | 21.9 | 21.4 | 21.1 |
| 700 nm | Average | 22 | 21.85 | 22.15 | 21.75 | 22.25 | 22 |
| | % | 100 | 99.3 | 101.4 | 98.2 | 102.3 | 98.9 |

To study the effect L-cystathionine (L-CYST) on the tHCY assay, three plasma samples containing low, medium and high concentrations of tHCY was spiked with L-CYST at 0.1, 0.2 and 0.5 mol/L. These L-CYST concentrations were added in addition to the L-CYST concentrations found in a normal plasma sample. The results, depicted below in Table 13, demonstrate that the L-CYST concentrations up to 0.5 mol/L only provide <5% cross reactivity in the tHCY assay. The samples were analyzed in quadruplicate by the tHCY assay. The results were calculated using the following formulas:

$$\frac{tHCY\ \mu mol/L\ (spiked\ sample - non\text{-}spiked\ sample)}{Actual\ concentration\ of\ added\ agents} \times 100 = \% \text{ cross-reactivity}$$

$$\frac{tHCY\ \mu mol/L\ (spked\ sample - non\text{-}spiked\ sample)}{tHCY\ \mu mol/L\ (non\text{-}spiked\ sample)} \times 100 = DF\ (\%)$$

TABLE 13

L-Cystathionine Cross-Reactivity in the Two-Reagent tHCY Assay

| | Spiked CYST (µmol/L) | Average HCY (µmol/L) | Ratio (%) | DF (%) |
|---|---|---|---|---|
| Sample-1 | 0 | 7.6 | 100 | 0 |
| | 100 | 7.3 | 96 | 4 |
| | 200 | 7.5 | 99 | 2 |
| | 500 | 7.3 | 96 | 4 |
| Sample-2 | 0 | 12.6 | 100 | 0 |
| | 100 | 12.3 | 98 | 2 |
| | 200 | 12.4 | 98 | 2 |
| | 500 | 12.4 | 98 | 2 |
| Sample-3 | 0 | 23.6 | 100 | 0 |
| | 100 | 23.5 | 100 | 1 |
| | 200 | 23.8 | 101 | 1 |
| | 500 | 24.1 | 102 | 2 |

The effects of L-Cysteine (L-CYS) interference on the tHCY assay was determined using three plasma samples containing low, medium and high concentrations of tHCY spiked with L-CYS. The spiked samples were prepared and analyzed in triplicate, Each of the three samples includes spiked L-CYS at concentrations of 0, 50 and 100 µmol/L. The cross reactivity and DF % were calculated. The results are provided below in Table 14. The results demonstrate that L-CYS concentrations up to 100 µmol/L only exhibit <10% cross reaction in the tHCY assay.

TABLE 14

L-Cysteine Cross-Reactivity in the Two-Reagent tHCY assay

| | Spiked CYS (µmol/L) | Average HCY (µmol/L) | Ratio (%) | DF (%) |
|---|---|---|---|---|
| Sample-1 | 0 | 7.6 | 100 | 0 |
| | 50 | 7.3 | 96 | 4 |
| | 100 | 7.0 | 92 | 7 |
| Sample-2 | 0 | 12.6 | 100 | 0 |
| | 50 | 12.6 | 100 | 0 |
| | 100 | 12.3 | 98 | 2 |
| Sample-3 | 0 | 23.6 | 100 | 0 |
| | 50 | 23.8 | 101 | 1 |
| | 100 | 22.3 | 94 | 6 |

The effects of L-methionine (L-MET) on the tHCY assay were studied using a protocol wherein three plasma samples containing low, medium and high concentrations of tHCY were spiked with L-MET. The concentrations of L-MET were 0.05, 0.1 and 0.2 mol/L. These concentrations of L-Met added to the plasma samples were in addition to the L-MET concentrations found in a normal plasma sample. The samples were analyzed in quadruplicate by the tHCY assay. The results provided below in Table 15 demonstrate that the L-MET concentrations up to 0.2 mol/L only impart <5% cross reaction in the tHCY assay.

TABLE 16

L-Methionine Cross Reactivity in the Two-Reagent tHCY Assay

| | Spiked L-MET (µmol/L) | Average HCY (µmol/L) | Ratio (%) | DF (%) |
|---|---|---|---|---|
| Sample-1 | 0 | 7.6 | 100 | 0 |
| | 50 | 7.3 | 96 | 4 |
| | 100 | 7.5 | 99 | 2 |
| | 200 | 7.3 | 96 | 4 |
| Sample-2 | 0 | 12.6 | 100 | 0 |
| | 50 | 12.3 | 98 | 2 |
| | 100 | 12.4 | 98 | 2 |
| | 200 | 12.4 | 98 | 2 |
| Sample-3 | 0 | 23.6 | 100 | 0 |
| | 50 | 23.5 | 100 | 1 |
| | 100 | 23.8 | 101 | 1 |
| | 200 | 24.1 | 102 | 2 |

While this disclosure has been described in conjunction with the specific embodiments outlined above, it is evident that many alternatives, modifications and variations will be apparent to those skilled in the art. Accordingly, the preferred embodiments of the present disclosure as set forth above are intended to be illustrative, not limiting. Various changes may be made without departing from the spirit and scope of the invention, as required by the following claims. The claims provide the scope of the coverage of the invention and should not be limited to the specific examples provided herein.

What is claimed is:

1. A method of measuring total homocysteine comprising the steps of:
    providing a sample containing homocysteine;
    reducing the homocysteine with a reducing agent;
    enzymatically reacting the homocysteine with homocysteinase (HCYase), producing hydrogen sulfide ($H_2S$);
    providing N,N-dibutyl-p-phenylenediamine-pyridoxal 5'-phosphate (DBPDA-PLP Schiff-base);

providing 300 mg of DBPDA (1.056 mmol) in 10 ml solution of anhydrous ethyl alcohol mixed with a 20 ml of PLP (336 mg, 1.26 mmol), releasing DBPDA from the DBPDA-PLP Schiff Base;

combining the DBPDA released from the DBPDA-PLP with the $H_2S$ in the presence of an Fe(III) containing compound producing at least one chromophore;

measuring the concentration of the at least one chromophore, wherein the measuring step comprises generating a standard curve correlating a concentration of the at least one chromophore with a known concentration of homocysteine; and determining the total concentration of homocysteine in the sample using the standard curve.

2. The method of claim 1, wherein the homocysteinase is L-homocysteine α,γ-lyase (rHCYase).

3. The method of claim 1, wherein the step of enzymatically reacting the homocysteine with HCYase, producing the $H_2S$, occurs in approximately five minutes.

4. The method of claim 1, wherein the step of combining the DBPDA released from the DBPDA-PLP with the $H_2S$ in the presence of the Fe(III) containing compound produces the at least one chromophore in approximately five minutes.

5. The method of claim 1, wherein the Fe(III) containing compound is $FeCl_3$.

6. The method of claim 1, wherein the reducing agent is dithiothreitol (DTT).

7. The method of claim 1, wherein the step of measuring the at least one chromophore is performed by measuring the chromophore's absorbance at approximately 660 nm.

8. The method of claim 1, wherein the step of measuring the at least one chromophore is performed by measuring an excitation spectrum of the chromophore's fluorescence at approximately 660 nm.

9. The method of claim 1, wherein the step of measuring the at least one chromophore is performed by measuring an emission spectrum of the chromophore's fluorescence at approximately 700 nm.

10. The method of claim 1, wherein the method is performed using a first reagent and a second reagent, wherein the first reagent comprises a reducing agent known to reduce disulfide bonds to sulfhydryl bonds, a homocysteinase enzyme, and a chromogenic agent capable of performing a reaction resulting in a chromophore product.

11. The method of claim 10, wherein the second reagent comprises an oxidant comprising any Fe(III) containing compound capable of oxidizing a pre-chromophore into a chromophore and a strong acid solvent selected from the group of strong acids consisting of: HI, HBr, $HClO_4$, HCl, $HClO_3$, $H_7SO_4$ and $HNO_3$.

\* \* \* \* \*